(12) United States Patent
Idoine et al.

(10) Patent No.: US 8,374,681 B2
(45) Date of Patent: Feb. 12, 2013

(54) APPARATUS AND METHOD FOR FUNCTIONAL NEUROLOGICAL SCREENING WITH ADJUSTABLE SPACED COLLIMATOR PLATES

(76) Inventors: John D. Idoine, Mount Vernon, OH (US); Harold T. Pretorius, Cincinnati, OH (US)

( * ) Notice: Subject to any disclaimer, the term of this patent is extended or adjusted under 35 U.S.C. 154(b) by 842 days.

(21) Appl. No.: 12/373,835

(22) PCT Filed: Jul. 16, 2007

(86) PCT No.: PCT/US2007/073611
§ 371 (c)(1),
(2), (4) Date: Jan. 14, 2009

(87) PCT Pub. No.: WO2008/009021
PCT Pub. Date: Jan. 17, 2008

(65) Prior Publication Data
US 2009/0285749 A1    Nov. 19, 2009

Related U.S. Application Data

(60) Provisional application No. 60/807,406, filed on Jul. 14, 2006.

(51) Int. Cl.
*A61B 6/00* (2006.01)
(52) U.S. Cl. .................................................. 600/436
(58) Field of Classification Search .................. 600/436, 600/431; 378/147, 150
See application file for complete search history.

(56) References Cited

U.S. PATENT DOCUMENTS

| | | | |
|---|---|---|---|
| 4,118,632 A * | 10/1978 | Luig | 250/363.1 |
| 4,465,540 A * | 8/1984 | Albert | 156/252 |
| 5,591,976 A * | 1/1997 | Berthold et al. | 250/363.1 |
| 5,638,817 A | 6/1997 | Morgan et al. | |
| 6,225,631 B1 | 5/2001 | Mastrippolito et al. | |
| 2004/0092809 A1 * | 5/2004 | DeCharms | 600/410 |
| 2005/0215889 A1 | 9/2005 | Patterson, II | |

* cited by examiner

*Primary Examiner* — Jacqueline Cheng
(74) *Attorney, Agent, or Firm* — Charles R. Wilson

(57) ABSTRACT

A variable focus collimator device and method for functional neurological screening. The variable focus collimator uses sets of corresponding holes in two plates of gamma shielding material, arranged so that only gamma rays emitted from a defined focal region detected. If a suitable radio-labeled tracer has been administered to the patient, this may be used to obtain and compare basal and stimulated data from a small number of regions in the brain to diagnose the presence or absence of dementias. The regions of the brain observer are typically about a cm cubed in volume, and their activity is monitored using small doses (<2 mCi) of radio-labeled, brain perfusion agents. The regions used are easily and repeatably located relative to well-known anthropological and radiological fiducials. By simply use of symmetry, ratios and cortical to cerebellar comparisons, rapid (~15 minute) screening for dementia may be accomplished.

11 Claims, 6 Drawing Sheets

APPARATUS AND METHOD FOR FUNCTIONAL NEUROLOGICAL SCREENING WITH ADJUSTABLE SPACED COLLIMATOR PLATES

CROSS REFERENCE TO APPLICATIONS

This application is related to, and claims priority from U.S. Provisional Patent application No. 60/807,406 filed on Jul. 14, 2006 by John D. Idoine and Harold T. Pretorius entitled "Method to Screen for Alzheimers's Disease and Other Dementias", the content of which is hereby incorporated by reference in it's entirety.

TECHNICAL FIELD

The present invention relates to the field of nuclear medicine. More specifically, the present invention relates to a method, apparatus, and system for functional neurological screening using a diverging or variable focus collimator to monitor radio-labeled tracers.

BACKGROUND ART

In the field of nuclear medicine, functional imaging of the human brain has yielded insight in to the early stages of various human dementias, including Alzheimer's Disease. Using well known techniques such as Positron Emission Tomography (PET) scanning and Single Photon Emission Computed Tomography (SPECT) imaging, researchers have, for instance, found specific patterns of brain activity, or signatures, characteristic of particular dementia. Early stage Alzheimer's Disease is characterized by a decrease in resting state, or basal, metabolic activity within certain regions of the cerebral cortex, which are diagnostic of Alzheimer's with an accuracy of 85% or better. Even greater accuracy is obtained using the knowledge that in early Alzheimer's, the same regions of compromised metabolic activity maintain their ability to increase blood flow, or perfusion, in response to stimulants. This Alzheimer's signature pattern of a positive effect of stimulants on cerebral perfusion but a compromised basal metabolism is particularly evident in areas such as the hippocampus (mesial temporal) and the parieto-occipital cortex.

In contrast, vascular dementia, which in theory may affect any vascular territory of the brain, often also affects the parieto-occipital cortex, which is essentially in a watershed territory between the major cerebral arteries contributing to the anterior and posterior cerebral circulation. The signature pattern of vascular dementia is opposite to Alzheimer's (or most other neurodegenerative disorders), in that cerebrovascular flow reserve, or the ability to demonstrate a positive response to a cerebral perfusion stimulant, is not only absent but typically compromised in cerebrovascular disease, which is most often responsible for vascular dementia. These signature patterns are potentially a very effective way to screen patients to detect the onset of Alzheimer's or vascular dementia at an early stage so that appropriate treatment may be administered before the disease process is more advanced and most therapies are less likely to be effective.

PET and SPECT scanning, which provide three dimensional information about brain metabolism and perfusion and can thus even distinguish the not infrequent patients with mixed patterns (eg. patients with a component of cerebrovascular disease predominating in one area and a component of Alzheimer's disease predominating in another area), are; however, time consuming and require very costly equipment and support infrastructure.

In PET scanning, the patient is given a short-lived radioactive tracer isotope that decays by emitting a positron. The radioactive isotope is chemically incorporated into a metabolically active molecule that is typically injected into the patient's blood circulation. After waiting typically about an hour for the molecule to become concentrated in the tissues of interest, the patient is placed in the imaging scanner. A commonly used molecule for brain scanning is $F^{18}$ (half-life 109 minutes) labeled 2-fluoro-2-Deoxyglucose (FDG), a sugar that can cross the blood-brain barrier. The positron particle derived from FDG in actually an anti-matter particle, that almost immediately collides with an electron (typically the most available normal matter). The resulting annihilation reaction yields two 511 keV gamma photons that are emitted in very nearly opposite directions. Using coincidence detectors with pico-second temporal resolution and sophisticated computers, the position of the original decay can be calculated to within a fraction of a millimeter. This also requires a correction for attenuation of the 511 keV gamma rays within the brain, skull and other tissues of the head, which is typically derived from a second set of measurements with another radioactive source, including more recently, an x-ray computerized tomographic (CT) scanner, which may be coupled into a single expensive (on the order of two million dollars) PET-CT instrument. The result is a three dimensional image of the activity in the brain (or other body part), whose resolution remarkably depends mainly on the few millimeters the original positron may have traveled before it encountered an electron.

SPECT imaging is a little less complex, using a gamma camera to acquire multiple two-dimensional images, or projections, from multiple angles. A computer is then used to apply a tomographic reconstruction algorithm to the multiple projections, yielding a three dimensional dataset. As with PET, attenuation of the emitted gamma ray may be corrected with a significant increased cost by combining another gamma ray source to produce another image of the density (with respect to gamma rays) of the scanned object, or a combined SPECT-x-ray CT scanner. Most SPECT cameras in routine use do not correct directly for attenuation, but may use a calculated attenuation correction, which is typically less accurate. The radioactive isotope typically used in SPECT imaging is technetium 99 (Tc-99), which decays by gamma emission, emitting 140 keV gamma rays. Tc-99 has a half-life of 6.02 hours, considerably longer than the 109 min half life of the $F^{18}$ FDG used in PET scanning. Moreover, it can be made in a relatively simple process from a source of decaying molybdenum-99 (Mo-99). Mo-99 has a half-life of 66 hours and can be easily transported over long distances to hospitals, while FDG is made in an expensive medical cyclotron and delivered directly to the scanning site. While the widespread delivery of $F^{18}$ is challenging, the growth of PET imaging for oncology and other uses has made it reasonably available throughout most of the United States and most other industrialized nations. Other PET tracers, such as those used for PET perfusion measurements have much shorter half-lives (eg. oxygen-15 labelled water with half-life about two minutes) and are only available in major medical or scientific centers.

Perhaps more important than the issue of attenuation corrections, which are imperfect but not so very important for measurements pertaining to a tissue such as the cortex of the brain, which is quite superficial (attenuation corrections are more critical for deeper structures) are related issues pertaining to background and scattered radiation. In this context background applies not only to minimal activity from natural sources such as cosmic rays, but also considerable activity from the various tissues in the head apart from the neuronal cells. Thus, activity from blood vessels, the pituitary gland, the skin and subcutaneous tissues, facial muscles and ependymal cells in the choroid plexus all contribute background activity which must be resolved from nearby neuronal activity. Most of these sources of background activity are outside the blood-brain barrier. Clearly, PET and SPECT tracers of cerebral perfusion and metabolism cross the blood brain barrier, but they are also present in the tissues outside the blood brain barrier. In fact, when first injected, the PET or SPECT tracers are entirely within the bloodstream. Depending on the patient's overall metabolism, a variable time (typically about an hour) passes before blood levels decrease to such an extent that they contribute only a small background to the brain image based mainly on perfusion and/or metabolism of the neuronal cells that is actually responsible for the recognizable patterns of activity in specific forms of dementia. Scattered radiation, related to incomplete absorption of gamma rays, specifically Compton scattering, is a principal factor degrading resolution of nuclear medicine images, even PET images that in part correct for this effect by the coincidence counting described above. While these sources of background are not such a problem as to negate the excellent results of PET and SPECT images which may correct for them to variable degrees, especially in research applications, practical ways to deal with them in everyday clinical applications would be a significant advance.

What is needed to make more practical use of the insights into brain function yielded by PET and SPECT imaging is a simple, low cost gamma radiation monitoring instrument capable of reliable measure of basal and stimulated activity within the cerebral cortex and other parts of the brain, using small and potentially inexpensive quantities of easily transported radioisotopes. Such an instrument, when applied with the appropriate methodology, may for instance, use the signature patterns discovered using PET and SPECT imaging as an effective way to screen populations to detect the onset of dementia. It would also be important if such an instrument would further enable increased accuracy without undue increased cost or inconvenience by simple approximations to background corrections which otherwise contribute to error in determining diagnostic patterns of neuronal activity.

This latter consideration becomes even more important in screening application where use of an oral tablet of FDG (known to have a very similar eventual bio-distribution as an injected dose of FDG) could be used to avoid the inconvenience of an injection, but at the expense of a longer and more variable time for absorption into, and subsequent clearance of the tracer from, the bloodstream. Moreover, an instrument allowing simultaneous measure of cerebral perfusion and metabolism, through the use of separate tracers in small amounts, would have significant advantages in recognition of cerebral patterns of activity as compared to PET, all of whose tracers produce the same 511 keV gamma rays and can therefore only be practicably measured sequentially, rather than simultaneously, or even SPECT, whose sensitivity and relatively low energy resolution are typically insufficient to permit widespread use of simultaneous dual tracer studies because of the risks of an increased radiation dose.

DISCLOSURE OF INVENTION

The present invention relates to methods and devices for functional neurological screening using a variable focus collimator to monitor radio-labeled tracers. Such a device allows simple, low cost gamma radiation monitoring that may, for instance, be used to easily and reliably measure basal and stimulated activity within the cerebral cortex and other parts of the brain using small quantities of easily transported radioisotopes. Such measurements may be, for instance, be used to screen patients for the onset of Alzheimer's and other dementia by detecting their signature functional brain activity patterns.

In a preferred embodiment, the variable focus collimator uses sets of corresponding holes in two plates of a gamma shielding material such as, but not limited to, a tungsten alloy or lead. The plates and the holes are arranged so that only gamma rays emitted from a defined focal region can reach a gamma detector, such as a photo-tube. If a suitable radio-labeled tracer has been administered to the patient, this simple arrangement may be used to obtain the measurements necessary for analyzing the brain by Correlative Brain Regional Activity (COBRA).

COBRA is a system and method for obtaining and comparing basal and stimulated data from a small number of regions in the brain to diagnose the presence or absence of dementias. The regions of the brain observed are typically about a cm cubed in volume, and their activity is monitored using small doses (<1 mCi) of radio-labeled, brain perfusion agents such as, but not limited to, Tc-99 labeled hexamethylpropylamine oxime (HMPAO) or ethylcysteine dimer (ECD). The regions used are typically easily and reproducibly located relative to well-known anthropological and radiological fiducials such as, but not limited to, the canthomeatal and acanthiomeatal lines. By simply use of symmetry, ratios and cortical to cerebellar comparisons, COBRA enables rapid (~15 minute) screening for dementia.

In one preferred use of COBRA, for instance, the basal peak cerebellar activity is compared to the basal peak cortical activity. This is done by monitoring activity in the rear of the head upwards from the acanthiomeatal line, along the center line, at a depth of approximately 2 cm beneath the skull to obtain the cortical peak, i.e., the peak activity in the cerebral cortex. The cerebellar peak is then found by monitoring activity in the rear of the head downwards from the acanthiomeatal line at a depth of approximately 3 cm and approximately 1 cm on either side of the center line. This locates the twin peaks of activity in the cerebellum. In a normal patient, the basal cortical peak is greater than the basal cerebellar peaks so that if this is reversed it is indicative of the onset of dementia.

These and other features of the invention will be more fully understood by references to the following drawings.

BEST MODE FOR CARRYING OUT THE INVENTION

The present invention relates to functional neurological screening using a variable focus collimator to monitor radio-labeled tracers.

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

Figure 1:
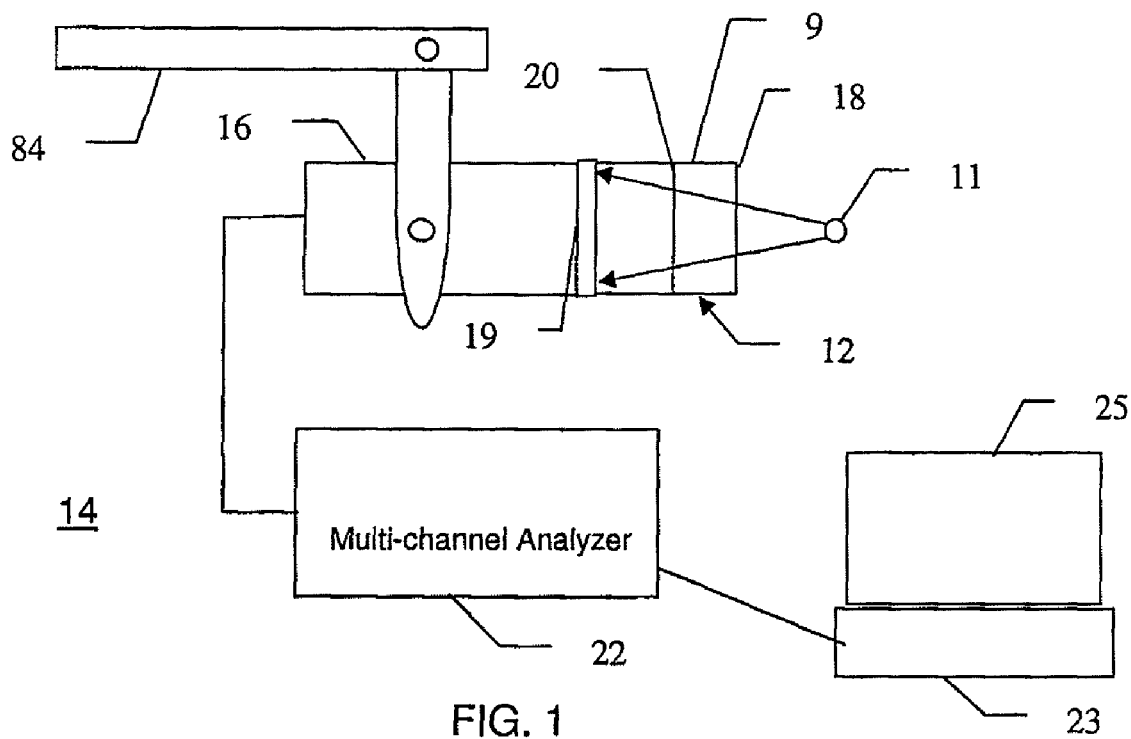
FIG. 1 shows a schematic view of an apparatus suitable for the functional neurological screening using a variable focus collimator of the present invention.

FIG. 1 shows a schematic view of a Cortical Brain Regional Activity (COBRA) probe 14 apparatus suitable for the functional neurological screening using a variable focus collimator of the present invention. The COBRA probe 14 may include a gamma ray detector 16, having a face plate 19, and a focusing collimator 12 that includes a front collimator plate 18 and a rear collimator plate 20. The COBRA probe 14 may also include a multi-channel analyzer 22 and a general purpose computer 23 with a display monitor 25. The COBRA probe 14 may also include a positioning support 84 that may be controlled entirely or in part by the general purpose computer 23. The focusing collimator 12 of the COBRA probe 14 causes photons effectively emitted from within a focal region 11 to be incident on the face plate 19 of the gamma ray detector 16.

The gamma ray detector 16 may be any suitable detector capable of detecting gamma rays emitted, or caused to be emitted, by the radio-labeled tracers typically used in standard radio-imaging. The gamma ray detector 16 may for instance be a NaI photomultiplier tube as supplied by, for instance, Canberra Industries, Inc. of Meriden, Conn. capable of detecting gamma rays in the energy range of 50 keV to 600 keV. The gamma ray detector 16 may instead be a diode type detector such as, but not limited to, a Cadmium Telluride (CdTe) diode detector as supplied by Amptex Inc, of Bedford, Mass.

The multi-channel analyzer 22 may be any suitable multi-channel analyzer capable of interconnecting with a standard gamma ray detector and capable of discriminating, for instance, between 140 keV gamma rays emitted by a technetium 99 (Tc-99) labeled radio isotope and the 70-80 keV gamma rays emitted by Thallium 201 isotopes. A suitable multi-channel analyzer 22 is, for instance, the MCA 8000A model supplied by Amptek Inc. of Bedford, Mass.

Figure 2:
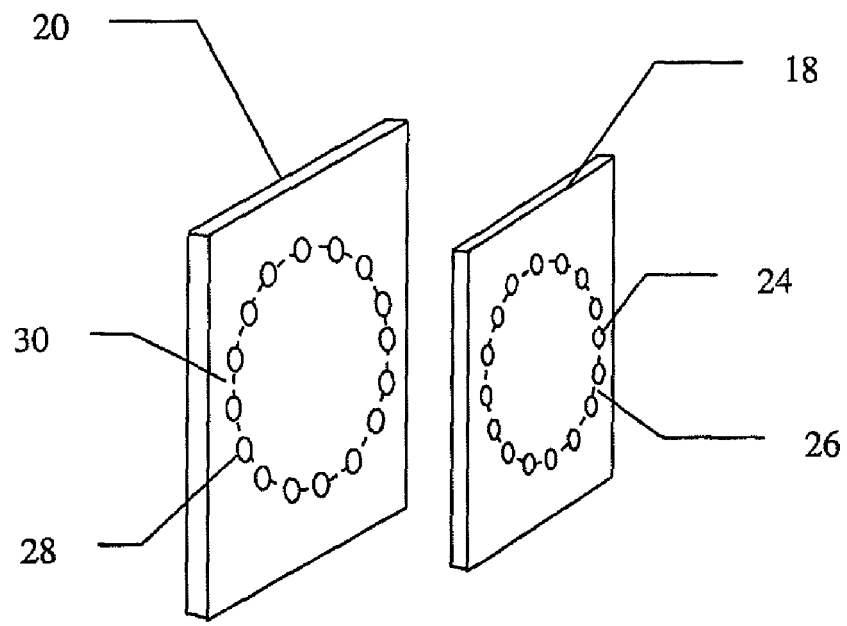
FIG. 2 shows a schematic, isometric view of a variable focus collimator of the present invention.

FIG. 2 shows a schematic, isometric view of the front collimator plate 18 and the rear collimator plate 20 of a variable focus collimator 12 of the present invention. The front collimator plate 18 and the rear collimator plate 20 are both made of a gamma shielding material, i.e., a material that is substantially opaque to gamma radiation having energies in the 50 to 200 keV range. A suitable gamma shielding material is a plate of lead a few millimeters thick. A preferred gamma shielding material is a millimeter thick plate of machinable tungsten alloy such as, for instance, the Kulite™ tungsten/copper alloy supplied by H. C. Starck of Goslar, Germany. The front collimator plate 18 has a series of front holes 24 drilled on a front pattern 26, while the rear collimator plate 20 has a corresponding series of rear holes 28 arranged on a rear pattern 30. In a preferred embodiment both the front pattern 26 and the rear pattern 30 are circles of different diameter. One of ordinary skill in the art, however, will appreciate that the front pattern 26 and the rear pattern 30 could be any one of a variety of corresponding shapes including, but not limited to, a plurality of circles, a conic section, a plurality of conic sections, a row, a rectangle, or even a random pattern as long as the front pattern 26 was an identical, but scaled down, copy of the rear pattern 30.

Figure 3:
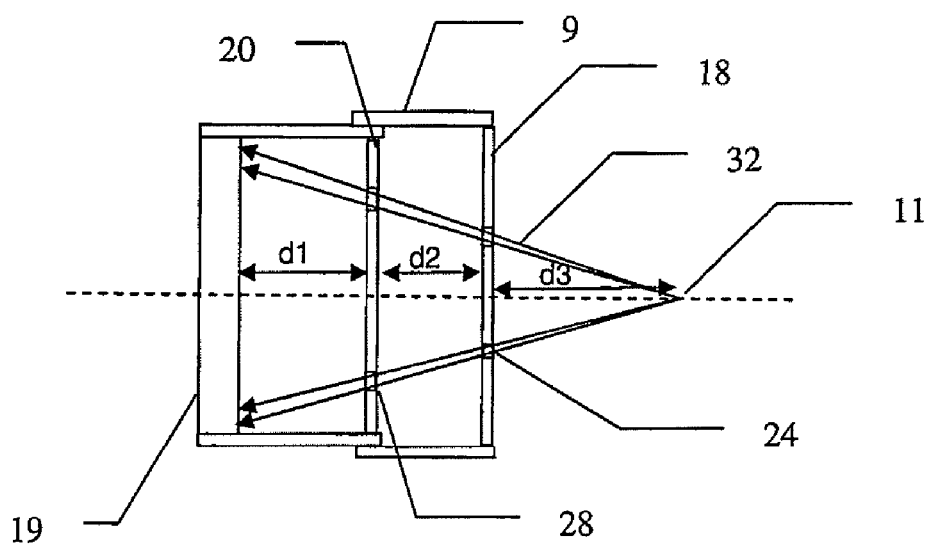
FIG. 3 is a schematic cross-section of a variable focus collimator of the present invention.

FIG. 3 is a schematic cross-section of the variable focus collimator 12 of the present invention showing a cone of rays 32 emanating from the focal region 11 and reaching the face plate 19 of the gamma ray detector 16.

In a preferred embodiment the front collimator plate 18 has the front holes 24 drilled on a front circle that is half the diameter of the rear circle on which the rear holes 28 are drilled. By making the ratio of the rear pattern 30 to the front pattern 26 to be 2:1, the distance d3 from the focal region 11 to the front collimator plate 18 is always equal to the distance d2 from the front collimator plate 18 to the rear collimator plate 20. In this way, as the front collimator plate 18 is moved to change the position of the focal region 11, it is easy for an operator to visualize where the focal region 11 is located.

In a preferred embodiment the rear holes 28 are made twice as large as the front holes 24 so that any gamma rays from the focal region 11 that pass through the front holes 24 will also pass through the rear holes 28. This tends to maximize collection of gamma rays from the focal region 11 while tending to minimize any background radiation emitted from outside the focal region 11. Additionally, background activity contributions may be determined by measurements of second tracer substances excluded from the blood brain barrier, including but not limited to: sodium iodine-123 (ideal for background secondary to the ependymal cells of the choroid plexus, which concentrate this tracer as well as Tc-99m-pertechnetate, which may be similarly used), thallium-201 chloride, or Tc-99m-Myoview (especially useful for scalp background). With sufficient shielding, the instrument may be modified for simultaneous use with FDG, which permits simultaneous measurements of stimulated perfusion (eg. using Tc-99m-HMPAO) and metabolism (using the FDG). Measurement and correction for separate contributions of the different isotopes to each other is part of prior art and familiar to anyone skilled in the field with the caveat that the standard corrections for downscatter of higher energy isotopes (eg. 511 keV PET tracers) contributing to apparent activity in lower energy signals (eg. the most frequent Tc-99m SPECT tracers) are as usual corrected not only for the different sensitivity of the particular detector system (eg. NaI crystal coupled to a multichannel analyzer) used with respect to specific energy level detected but also need to be further corrected for time-dependent variability of the relative tracer uptakes by comparison to appropriate SPECT or PET studies of the relative uptake ratios of the tracer sets employed. While complex in principle, such corrections often reduce to remarkable simplifications in practice: eg. using a simple diverging collimator with a 9 mm aperture and Tc-99m-Myoview as the tracer to determine scalp background, the individual cortical activities measured at usual imaging times (near an hour after tracer injections) correlated remarkably well with measured SPECT cortical activities using a flat 20% background of peak cortical activity. While the 9 mm diverging collimator assessed a somewhat larger than optimal cortical area, another widely available embodiment of the invention, using a 3 mm pinhole in the bottom of a standard approximately 10 mm thick lead pig used to calibrate gamma cameras, placed on top of a standard well counter, and used inferior to patients who are positioned using an adjustable-height patient imaging table, is sensitive to a smaller cortical area more similar to that of the preferred embodiment using a variable focus collimator and similarly readily amenable to background corrections. The rear collimator plate 20 and the front collimator plate 18 are attached to the face plate 19 of the gamma ray detector 16 by an alignment structure 9 that allows the distance d2 of the front collimator plate 18 to the rear collimator plate 20 to be varied. The alignment structure 9 may, for instance, be two tubes that are slidably connected to each other. The alignment structure 9 may alternately be two tubes that have a screw connection that allows the distance d2 to be varied. In a further embodiment, the distance d1 may also be varied by having the alignment structure 9 slideably or screwably connected to the face plate 19.

In a preferred embodiment the rear holes 28 are made twice as large as the front holes 24 so that any gamma rays from the focal region 11 that pass through the front holes 24 will also pass through the rear holes 28. This tends to maximize collection of gamma rays from the focal region 11 while tending to minimize any background radiation emitted from outside the focal region 11.

Figure 4:
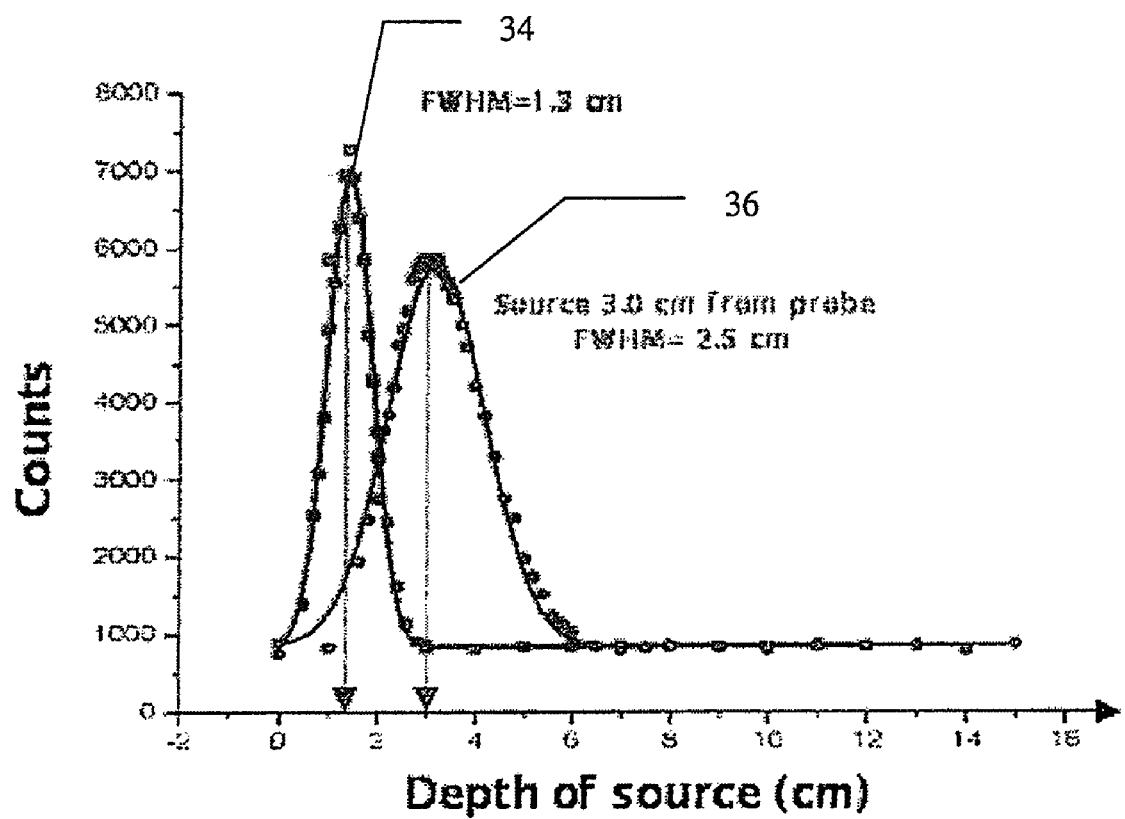
FIG. 4 is a graph showing experimental results obtained using a variable focus collimator of the present invention.

FIG. 4 is a graph showing experimental results obtained using a variable focus collimator of the present invention. The focusing collimator 12 used to produce the results of FIG. 4 had a gamma ray detector 16 that was a 6 inch diameter NaI phototube, and a front collimator plate 18 and a rear collimator plate 20 that were each 4 mm thick sheets of lead. The front holes 24 were about 3 mm in diameter. Both the front holes 24 and the rear holes 28 were drilled at an angle, although this is not required when using the thinner tungsten alloy sheets.

For the first graph 34, the front collimator plate 18 was positioned 1.3 cm in front of the rear collimator plate 20. A point source of radiation was then moved axially way from the center of the front collimator plate 18. The first graph 34 represents the photomultiplier counts as a function of the point source's distance from the front collimator plate 18. The first graph 34 shows that with the focal region 11 located 1.3 cm from the front collimator plate 18, the full width, half maximum (FWHM) is also 1.3 cm, i.e., the depth of the focal region 11 is approximately equal to the location of the center of the focal region 11.

For the second graph 36, the front collimator plate 18 was positioned 2.5 cm in front of the rear collimator plate 20. A point source of radiation was then moved axially way from the center of the front collimator plate 18. In second graph 36 the FWHM was 2.5 cm, i.e., the depth of the focal region 11 is still approximately equal to the location of the center of the focal region 11.

Figure 5:
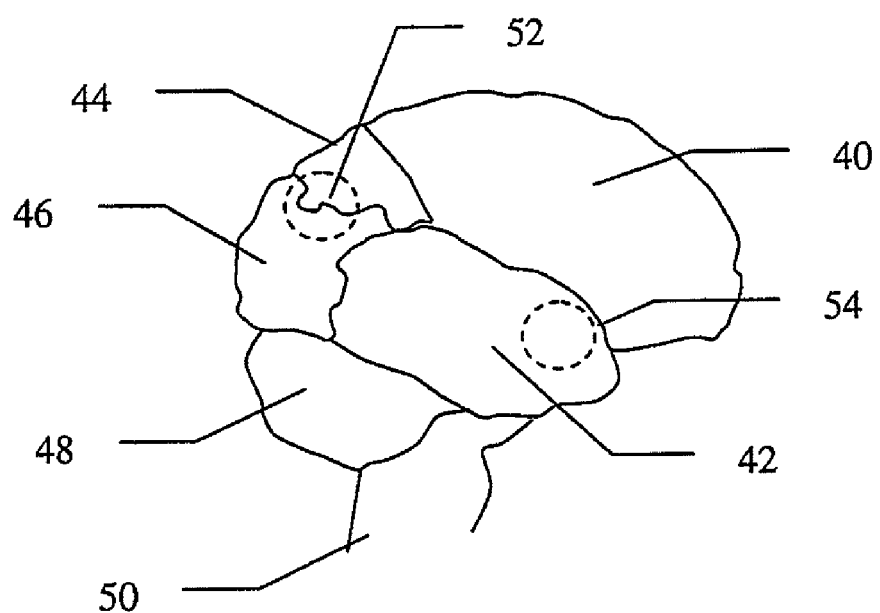
FIG. 5 is a schematic, saggital view of a typical adult human brain.

FIG. 5 is a schematic, saggital view of the surface of a typical adult human brain showing some of the well known regions of the brain and two regions of interest in COBRA analysis.

The adult brain may be divided into the frontal lobe 40, the temporal lobe 42, the parietal lobe 44, the occipital lope 46, the cerebellum 48, and the spinal cord 50. The frontal lobe 40, the temporal lobe 42, the parietal lobe 44 and the occipital lope 46 are all part of the cerebral cortex that is approximately 2-4 cm thick, is located just beneath the skull and plays a central role in complex brain functions such as memory, attention, perceptual awareness, thinking, language and consciousness. The cerebellum 48 is a region of the brain that plays an important role in the integration of sensory perception and motor output.

A first region of interest in COBRA screening for dementia is the olfactory cortex 54 that is located near the enthorhinal cortex in the mesial temporal lobe 42. This is a region in which the Alzheimer's signature pattern of a positive effect of stimulants on cerebral perfusion but a compromised basal metabolism is particularly evident.

A second region of interest in COBRA screening for dementia is the parieto-occipital cortex 52. This is another region in which the Alzheimer's signature pattern of a positive effect of stimulants on cerebral perfusion but a compromised basal metabolism is particularly evident.

The cerebellum 48 is also of interest in COBRA screening for dementia, primarily as a reference against which the strength of other regions of activity can be compared, as explained in more detail below.

Figure 6:
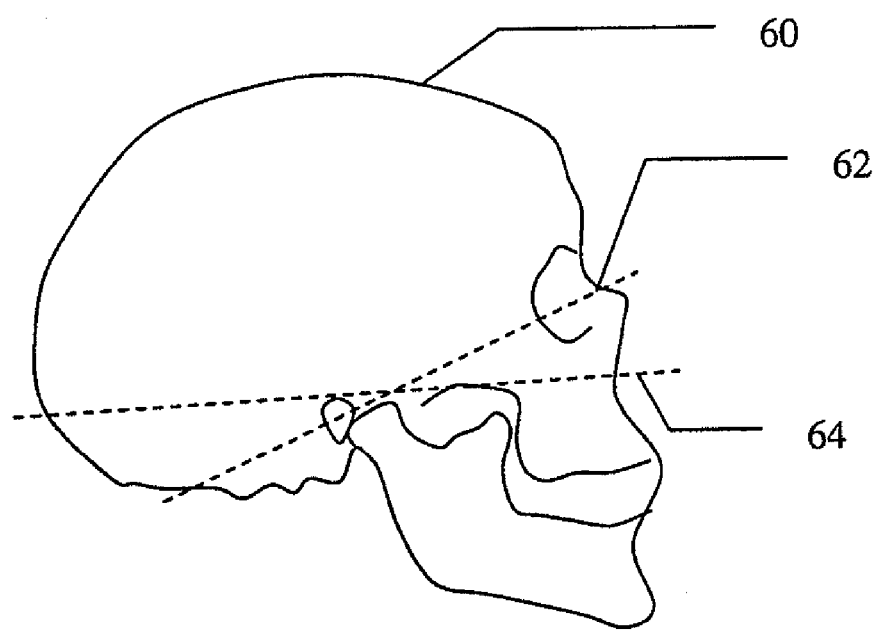
FIG. 6 is a schematic, saggital view of a typical adult human skull.

FIG. 6 is a schematic, saggital view of a typical adult human skull 60 showing two well-known anthropological and radiological fiducials, the canthomeatal line 62 and the acanthiomeatal line 64. The canthomeatal line 62 is an imaginary line that extends from center of the ear canal to the junction of the upper and lower eyelids. The acanthiomeatal line 64 is an imaginary line that extends from the outside of the ear canal to the center of the base of the front nasal spine. A full upper denture is typically constructed so that the teeth close parallel to this line.

Figure 7:
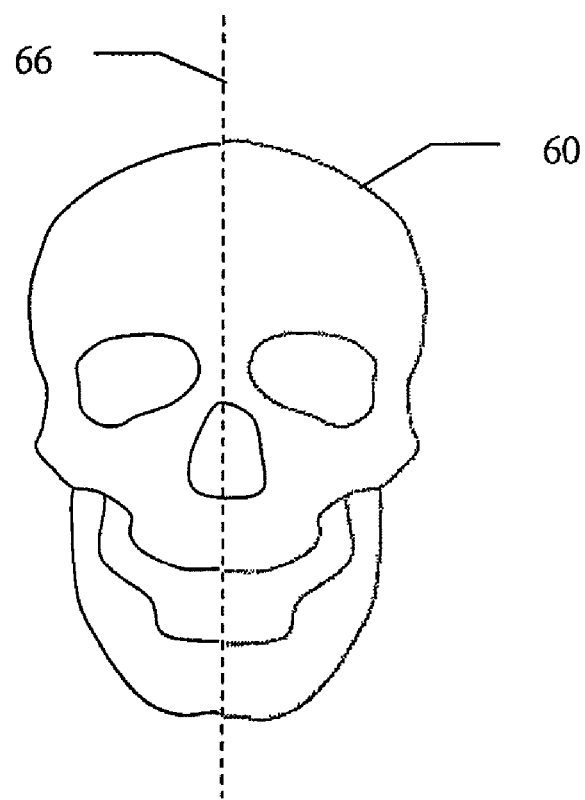
FIG. 7 is a schematic, front view of a typical adult human skull.

FIG. 7 is a schematic, front view of a typical adult human skull 60 showing the mid-line 66.

Figure 8:
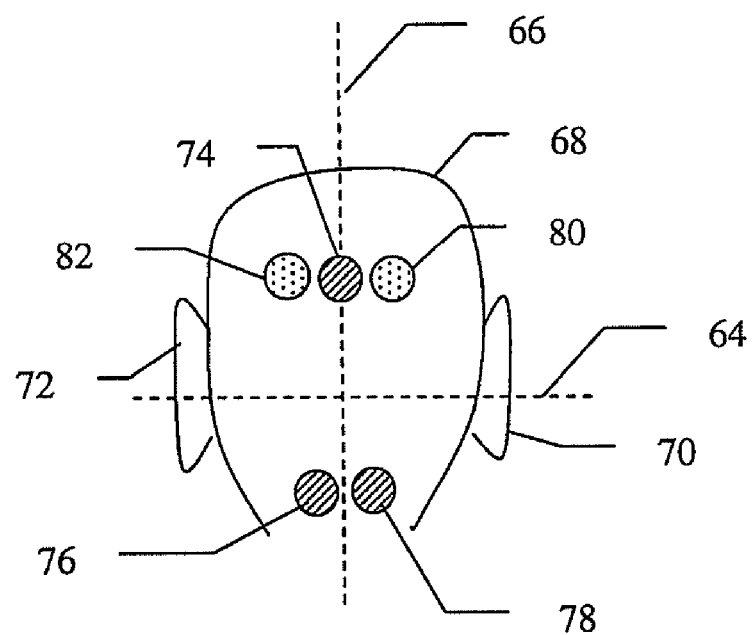
FIG. 8 is a schematic, rear view of a head of human patient showing some regions of interest in the COBRA method of the present invention.

FIG. 8 is a schematic, rear view of a head of human patient 68 showing some regions of interest in the COBRA method of the present invention.

A region of peak cortical activity 74 is typically located in the cerebral cortex at the junction of the parietal lobe 44 and the occipital lope 46. This means that it is typically on the mid-line 66 about 3 to 4 cm above the acanthiomeatal line 64. Being in the cerebral cortex the center of activity is typically about 2 cm beneath the skull. A few cm to each side of the region of peak cortical activity 74 are a left parieto-occipital cortex 82 and a right parieto-occipital cortex 80. Both the left and right parieto-occipital cortex show a compromised basal metabolism in early Alzheimer's patients, with the basal activity being reduced to about 80% of the activity in the region of peak cortical activity 74. On simulation by ingestion of, for instance, omega-3-unsaturated ethyl esters (Omacor), function in the left and right parieto-occipital cortex of Alzheimer's patients is restored to substantially the same level as in the region of peak cortical activity 74.

A left region of peak cerebellar activity 76 and a right region of peak cerebellar activity 78 are located in the cerebellum 48 about 1 cm to either side of the mid-line 66, about 3 cm below the acanthiomeatal line 64 and about 3 cm below the skull. In normal patients the basal activity of the left region of peak cerebellar activity 76 is substantially equal to the right region of peak cerebellar activity 78. In addition the regions of peak cerebellar activity 76 have lower activity than the region of peak cortical activity 74. In Alzheimer's patients the regions of peak cerebellar activity 76 have higher activity than the region of peak cortical activity 74. So these easily found peaks of activity may be used as a screening test for Alzheimer's. Importantly, in stroke patients, the basal activities of the left and right regions of peak cerebellar activity differ significantly.

Figure 9:
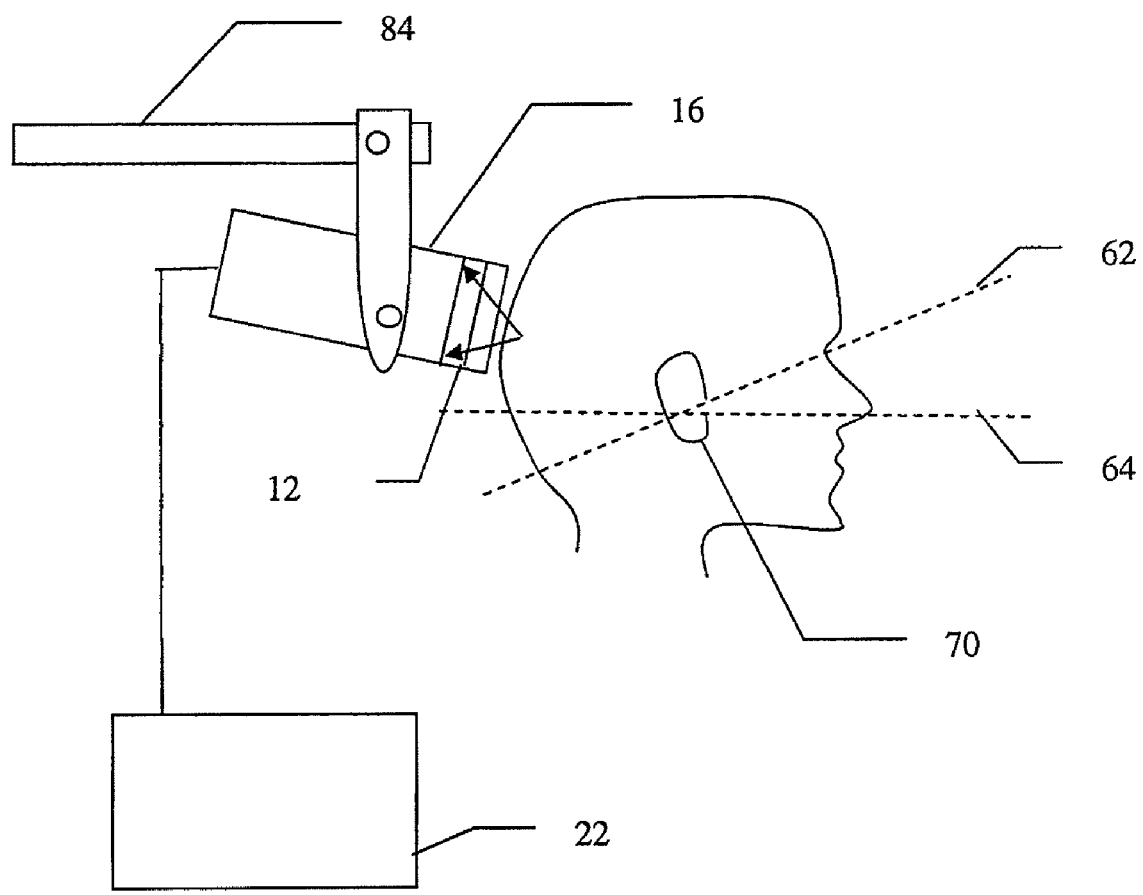
FIG. 9 is a schematic, side view of a head of a human patient undergoing functional neurological screening using the present invention.

FIG. 9 is a schematic, side view of a head of a human patient undergoing functional neurological screening using the present invention.

The patient may be administered a small dose of a radio-labeled, brain perfusion agent such as, but not limited to, Tc-99 labeled hexamethyo-propylamine oxime (HMPAO) or ethylcysteine dimmer (ECD). These agents cross the blood-brain layer and may be used to measure activity within the brain. The dosage needed to obtain good results with a COBRA probe 14 are less than 2 mCi and more typically as low as 800 µCi to 50 µCi. These doses are significantly less than the 10-20 mCi typically used in PET or SPEC scanning. The low dosage is possible, in part, because radiation is being gathered from a volume of brain that is about 2 cm$^3$ rather than from a point source.

The focusing collimator 12 of the COBRA probe 14 may then be set so that the focal region 11 is located about 2 cm below the surface of the patents skull.

The COBRA probe 14 may then be moved up the mid-line 66 starting from the acanthiomeatal line 64 to locate the region of peak cortical activity 74. From this point the COBRA probe 14 may be moved laterally to locate the left parieto-occipital cortex 82 and the right parieto-occipital cortex 80 to compare the activity there to the activity at the region of peak cortical activity 74. If it is significantly less, i.e., down to about 80%, that is a strong indicator of Alzheimer's.

The COBRA probe 14 may then be refocused to be about 3 cm below the patent's skull by moving the front collimator plate 18 a cm further away from the rear collimator plate 20. The COBRA probe 14 may then be moved down, and a cm to the left of the mid-line 66 starting from the acanthiomeatal line 64 in order to find the left region of peak cerebellar activity 76. If basal activity in the left region of peak cerebellar activity 76 exceeds the activity of the region of peak cortical activity 74, this is further indicative of Alzheimer's. In order to check, however, that the patent has not previously suffered a stroke, the right region of peak cerebellar activity 78 should then be found. These two areas of peak activity should be substantially equal in a non-stroke patient.

The patent may then be administered a suitable stimulant such as, but not limited to, omega-3-unsaturated ethyl esters (Omacor), and the procedures to find activity in the region of peak cortical activity 74, left parieto-occipital cortex 82 and right parieto-occipital cortex 80 repeated. If these activities are now substantially equal, it is highly likely that the patient is in the early stages of Alzheimer's, and further, considerably more expensive testing, such as a full PET or SPECT scan, may now be justified.

Other suitable cerebral stimulants include, but are not limited to, carbon dioxide inhalation, 500 mg to 1000 mg intravenous acetalzoamide, sublingual nitroglycerin with or without hand-grip or cold-pressor simulation and the oral ingestion of saturated fat.

The measurements may be further improved by using standard methods of biological background subtraction. For instance, in addition to the Tc-99 labeled HMPAO or ECD that crosses the blood-brain barrier, the patient may also be administered a suitable dose of a brain excluded tracer that emits gamma rays of a different energy, such as, but not limited to Thallium 201. The activity from the Thallium may then subtracted from the Tc-99 activity after making suitable allowance for any difference in sensitivity of the gamma ray detector 16 to the different energies of the gamma rays being detected. Improvements to the measurement may also be made by careful accounting of any down-scattering from one energy range to the other, as is well known in the art.

In a further embodiment of the invention, the COBRA probe 14 may be used on a patient administered with a simultaneous measure of cerebral perfusion and metabolism, through the use of separate tracers in small amounts. This has a marked improvement in recognition of cerebral patterns of activity compared to, for instance, PET in which all of whose tracers produce the same 511 keV gamma rays and in which cerebral perfusion and metabolism tracers may only practicably be measured sequentially, rather than simultaneously. Even SPECT, whose sensitivity and relatively low energy resolution are typically insufficient to permit widespread use of simultaneous dual tracer studies is not often used in this mode because of the risks of an increased radiation dose.

Figure 10:
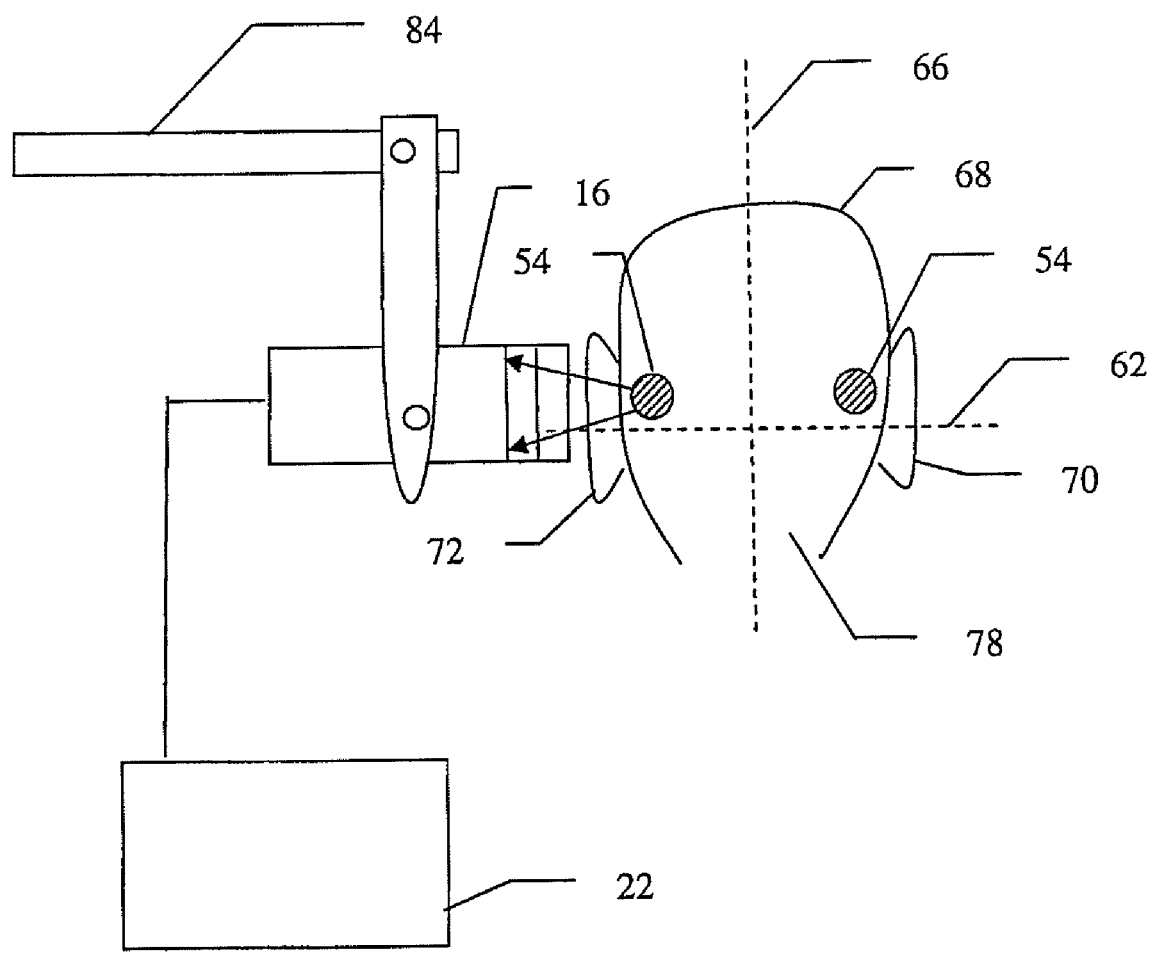
FIG. 10 is a schematic, rear view of a head of a human patient undergoing functional neurological screening using the present invention.

FIG. 10 is a schematic, rear view of a head of a human patient undergoing functional neurological screening using the present invention.

The COBRA probe 14 is now used to measure basal and stimulated activity in the both the left and right olfactory cortex 54. This may be done by positioning the COBRA probe 14 using the positioning support 84 perpendicular to the plane of the mid-line 66, and just forward of the left ear 72 about a cm above the canthomeatal line 62. The focusing collimator 12 may then be used to detect the basal, peak activity of the left olfactory cortex 54 and then the basal, peak activity of the right olfactory cortex 54. These measurements may then be repeated from the right side, near the right ear 70. These results may then be compared to the region of peak cortical activity 74 to see if they are comparable or diminished.

After administering the patient a suitable stimulant, the experiments may then be repeated to see if any dimension has been reversed, which would be a strong indicator of Alzheimer's.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

INDUSTRIAL APPLICABILITY

In the field of medical radiology, there is significant interest in functional neurological screening. Such measurements may be, for instance, be used to screen patients for the onset of Alzheimer's and other dementia by detecting their signature functional brain patterns.

What is claimed:

1. A method of functional neurological screening, said method comprising the steps of:
   a) administering a radio-labeled tracer to a patient;
   b) locating a first collimator plate having a plurality of openings arranged on a first pattern at a first predetermined position relative to a radiological fiducial of said patient;

c) placing a second collimator plate having a plurality of openings arranged on a second pattern at an adjustable spaced first predetermined distance from said first collimator plate, wherein the first pattern is a scaled down identical pattern to the second pattern;

d) placing a gamma detector a second predetermined distance from said second collimator, thereby detecting gamma radiation emitted by radioactive decay of said radio-labeled tracer from a first region of said brain of said patient comprising a region of peak cortical activity;

e) obtaining a first measurement representative of activity within said first region of said brain using said detected gamma radiation;

f) repeating steps a) to e) using a second predetermined position, thereby obtaining a second measurement representative of activity within a second region of said brain, said second region being (1) a region of peak cerebellar activity, (2) a region of parieto-occipital cortex, or (3) a region of olfactory cortex;

g) administering a stimulant to said patient;

h) repeating steps a) to e) after administering said stimulant using said first and second predetermined distances, thereby obtaining a third measurement representative of activity in said first region after stimulation and fourth measurement representative of said second region after stimulation; and i) obtaining an indicator of dementia by comparing said first and second measurement and comparing said third and fourth measurement.

2. The method of claim 1 wherein the first pattern is a first circle and wherein said second pattern is a second circle having a larger diameter than said first circle.

3. The method of claim 2 wherein said second circle has a diameter that is substantially equal to twice the diameter of said first circle.

4. The method of claim 1 wherein said second region is the region of peak cerebellar activity and wherein said indicator of dementia is of Alzheimer's disease if said second measurement is substantially greater than said first measurement, but said forth measurement is substantially less than said third measurement.

5. The method of claim 1 wherein said second region is the parieto-occipital cortex and wherein said indictor of dementia is of Alzheimer's disease if said second measurement is substantially less than said first measurement.

6. The method of claim 5 wherein said indictor of dementia is highly likely Alzheimer's disease if said second measurement is substantially less than said first measurement and said third measurement is substantially the same as said forth measurement.

7. The method of claim 1 wherein said second region is the olfactory cortex and wherein said indictor of dementia is strongly Alzheimer's disease if said first measurement is substantially less than said second measurement and said third measurement is substantially the same as said forth measurement.

8. A device for functional neurological screening of selected focal regions of a patient's brain, comprising:

a) first collimator plate having a thickness of from about one mm to about four mm and plurality of openings arranged on a first pattern;

b) a second collimator plate having a thickness of from about one mm to abut four mm and having a plurality of openings arranged on a second pattern wherein the first pattern of openings on the first collimator plate and the second pattern of openings on the second collimator plate have corresponding shapes and further wherein the first pattern of openings is an identical scaled down version of the second pattern of openings;

c) an alignment structure connecting the first collimator plate and the second collimator plate at a spaced distance in a manner such that the separation between said second collimator plate and said first collimator plate can be varied for creating a collimating focusing effect on one of the selected focal regions of the patient's brain; and d) a gamma detector attached behind said second collimator plate, thereby enabling detection of gamma radiation emitted from within the selected focal region of said device.

9. The method of claim 8 wherein said first pattern is a first circle and wherein said second pattern is a second circle having a larger diameter than said first circle.

10. The method of claim 9 wherein said second circle has a diameter that is substantially equal to twice the diameter of said first circle.

11. A method of functional neurological screening, said method comprising the steps of:

a) administering a radio-labeled tracer to a patient;

b) locating a first collimator plate having a plurality of openings arranged on a first pattern at a first predetermined position relative to a radiological fiducial of said patient;

c) placing a second collimator plate having a plurality of openings arranged on a second pattern that is larger than the first pattern at an adjustable spaced first predetermined distance from said first collimator plate;

d) placing a gamma detector a second predetermined distance from said second collimator, thereby detecting gamma radiation emitted by radioactive decay of said radio-labeled tracer from a first region of said brain of said patient comprising a region of peak cortical activity;

e) obtaining a first measurement representative of activity within said first region of said brain using said detected gamma radiation;

f) repeating steps a) to e) using a second predetermined position, thereby obtaining a second measurement representative of activity within a second region of said brain comprising a region of peak cerebellar activity;

g) obtaining an indicator of dementia by comparing said first and said second measurements;

h) administering a stimulant to said patient; and i) repeating steps a) to e) after administering said stimulant using said first and second predetermined distances, thereby obtaining a third measurement representative of activity in said first region after stimulation and a fourth measurement representative of said second region after stimulation, and wherein said step of obtaining an indicator of dementia further comprises comparing said third and said fourth measurement, wherein said indicator of dementia is of Alzheimer's disease if said second measurement is substantially greater than said first measurement, but said fourth measurement is substantially less than said third measurement.

* * * * *